(12) United States Patent
Tomie

(10) Patent No.: US 6,954,266 B2
(45) Date of Patent: Oct. 11, 2005

(54) METHOD AND APPARATUS FOR INSPECTING MULTILAYER MASKS FOR DEFECTS

(75) Inventor: Toshihisa Tomie, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/263,699

(22) Filed: Oct. 4, 2002

(65) Prior Publication Data

US 2003/0067598 A1 Apr. 10, 2003

(30) Foreign Application Priority Data

Oct. 5, 2001 (JP) .................................... 2001-309981

(51) Int. Cl.[7] .............................................. G01N 21/88
(52) U.S. Cl. ............................... 356/237.1; 236/237.1; 250/492.2
(58) Field of Search ...................... 356/237.1–327.6; 250/492.2; 378/33–34, 43, 70, 84–85, 145; 359/859, 861, 355, 366

(56) References Cited

U.S. PATENT DOCUMENTS

| 4,598,997 A | | 7/1986 | Steigmeier et al. |
| 4,749,840 A | * | 6/1988 | Piwczyk ................ 219/121.68 |
| 4,913,524 A | * | 4/1990 | Kreuzer ....................... 359/559 |

(Continued)

FOREIGN PATENT DOCUMENTS

| JP | 3-206944 | | 9/1991 | |
| JP | 06-349715 | | 12/1994 | |
| JP | 08179098 A | * | 7/1996 | ............ G21K/1/00 |
| JP | 10-221500 | | 8/1998 | |
| JP | 11-219891 | | 8/1999 | |
| JP | 11-354404 | | 12/1999 | |
| JP | 2000-171227 | | 6/2000 | |
| JP | 2001-116900 | | 4/2001 | |

OTHER PUBLICATIONS

G. D. Kubiak. et al. Journal of Vacuum Science & Technology. vol. 12. No. 6. pp. 3820–3825, XP–000497186. "Characterization of an Expanded–Field Schwarzschild Objective for Extreme Ultraviolet Lithography", Nov./Dec. 1994.

M. Yi, et al., J. Vac. Sci. Technol. B., vol. 18, No. 6, pp. 2930–2934, "Characterization of Extreme Ultraviolet Lithography Mask Defects From Extreme Ultraviolet Far–Field Scattering Patterns", Nov./Dec. 2000.

Journal of Vacuum Science & Technology B, American Vacuum Society, Nov./Dec. 2000, vol. 18, No. 6.

*Primary Examiner*—Gregory J. Toatley, Jr.
*Assistant Examiner*—Sang H. Nguyen
(74) *Attorney, Agent, or Firm*—Oblon, Spivak, McClelland, Maier & Neustadt, P.C.

(57) ABSTRACT

A method for inspecting multilayer masks to detect any defects includes illuminating a pixel region on a mask to be inspected, using illuminating light having a peak wavelength that is close to that of light reflected by the mask. The illuminating light specularly reflected by the mask is blocked. Scattered reflected illuminating light is collected and used to form an enlarged image. An image detector having a large plurality of pixels is used to observe the enlarged image to detect whether there are defects on the mask. The method is implemented using an mask inspection apparatus including a plasma light source for generating radiant rays, an illuminating light collecting optical system that collects radiated light from the light source for enlarged image formation illumination of a subject inspection region, a Schwarzschild optical system including convex and concave mirrors for collecting scattered light from the subject inspection region and forming an enlarged image of the inspection region, an image detector having a large plurality of pixels for recording the enlarged image that is obtained, and an analyzer that analyzes the images obtained to determine whether there is a defect.

8 Claims, 2 Drawing Sheets

U.S. PATENT DOCUMENTS

| | | | | |
|---|---|---|---|---|
| 5,022,064 A | * | 6/1991 | Iketaki | 378/145 |
| 5,131,023 A | * | 7/1992 | Yasugaki et al. | 378/43 |
| 5,132,994 A | * | 7/1992 | Kato | 378/43 |
| 5,144,497 A | * | 9/1992 | Kato et al. | 359/859 |
| 5,159,199 A | * | 10/1992 | LaBaw | 250/339.02 |
| 5,177,774 A | * | 1/1993 | Suckewer et al. | 378/43 |
| 5,264,912 A | | 11/1993 | Vaught et al. | |
| 5,291,339 A | * | 3/1994 | Mochimaru et al. | 359/859 |
| 5,528,646 A | * | 6/1996 | Iketaki et al. | 378/43 |
| 5,737,137 A | * | 4/1998 | Cohen et al. | 359/859 |
| 5,808,312 A | | 9/1998 | Fukuda | |
| 6,084,664 A | * | 7/2000 | Matsumoto et al. | 356/237.4 |
| 6,162,577 A | | 12/2000 | Felter et al. | |
| 6,522,717 B1 | * | 2/2003 | Murakami et al. | 378/43 |
| 6,590,165 B1 | * | 7/2003 | Takada et al. | 174/266 |
| 6,625,251 B2 | * | 9/2003 | Takenaka et al. | 378/84 |

* cited by examiner

METHOD AND APPARATUS FOR INSPECTING MULTILAYER MASKS FOR DEFECTS

BACKGROUND OF THE INVENTION

1. Field of the Invention

The present invention relates to a method for inspecting lithography multilayer masks for small defects, and to a defect inspection apparatus using the method.

2. Description of the Prior Art

Extreme ultraviolet (EUV) lithography (EUVL), in which an EUV light of 13 nm wavelength is employed as an illumination light, is the most promising lithography candidate for fabricating integrated circuits with a feature size of 70 nm or below. As such, related technologies are being developed.

One such technology that needs to be developed is that of inspection of defects on a mask. Since all materials absorb EUV light strongly, EUVL utilizes a reflection mask. To obtain high reflectance for EUV light, a multilayer structure consisting of several tens of pairs of layers of Si and Mo, each approximately 3-nm thick, are formed by vapor deposition on an optical device surface. An EUVL mask is a reflective mask on top of the multilayer reflector on which the device circuit pattern is defined by depositing absorbing material, and the size of the mask is about 140 mm by 140 mm. It is considered necessary to detect defects having a size of the order of 30 nm.

In existing lithography technologies, in which ultraviolet lasers are used as the light source, transmission type masks are employed and they are inspected using a visible laser-beam illumination. There have also been attempts to use laser-beam illumination in the case of EUVL reflective masks. However, the fact that the patterns to be inspected are becoming smaller, and that there is not much difference between the reflectance of the substrate Mo/Si multilayer and that of the absorbing material that is to be inspected for pattern defects, makes it difficult to inspect reflective masks for defects by a visible layer. This is explained in further detail, as follows.

When we designate $R_{def}$ as the reflectance (transmittance) of the defect that is tile target of the inspection, and the $S_{def}$ as the defect area and $R_{pix}$ as the background reflectance (transmittance), and $S_{pix}$ as the area thereof (pixel size), when a mask is illuminated by a photon density n, the amplitude of a signal $I_{def}$ when there is a defect, and of a signal $I_{pix}$ when there is no defect, will be as follows:

$$I_{def}=nR_{def}S_{def}+nR_{pix}(S_{pix}-S_{def}), I_{pix}=nR_{pix}S_{pix}$$

To be able to discriminate the two signals with sufficient accuracy, the difference between the signal amplitudes is to be at least three times larger than the shot-noise standard deviation σ, thus:

$$|I_{def}-I_{pix}|\geq 3(I_{def})^{1/2}+3(I_{pix})^{1/2}$$

Therefore, $$|(I_{def})^{1/2}-(I_{pix})^{1/2}|\geq 3$$

As such, the requisite number of photons is as follows.

$$(nS_{def})^{1/2}\geq 3R_{pix}^{1/2}((R_{def}/R_{pix})+(S_{pix}/S_{def}-1))^{1/2}+(S_{pix}/S_{def})^{1/2}/(R_{def}-R_{pix}) \quad (1)$$

With respect to visible light and ultraviolet light, a Mo/Si multilayer reflector acts as a metal reflector, and the mask pattern is also metal, so there is not much difference in reflectance between the two. The difference in reflectance is particularly small in the case of far ultraviolet light of wavelength 200 nm or below. For example, assuming a defect reflectance of $R_{def}=0.54$ and a background substrate mask reflectance of $R_{pix}=0.39$, if the target defect size is 30 nm and the pixel size is 200 nm, from equation (1), we get the following.

$$(nS_{def})\geq 27,800 \quad (2)$$

When the number of photons needed for illumination is 28,000, because the area of a 140 mm by 140 mm size mask is 2 E13 times of the defect area $S_{def}$, the number of photons needed to illuminate the whole mask will be 6E17. If the energy of one photon is 6 eV, the total energy would be 0.6 J. In order to complete inspection of the whole mask in three hours, if a total exposure time of one hour is allowed, an average illumination power of 0.2 mW would be required.

Under the above conditions, $I_{def}=486,000$ and $I_{pix}=481,000$, then, the difference between which is merely 1%. If the substrate is perfectly uniform, such as in the case of a Si wafer, inspection at the above power is possible, but in the case of a lithography mask on which complex patterns are formed, the intensity of reflection from the mask could well vary in the order of a percentage depending on location. This means that determining the presence or absence of defects necessitates complex processing by taking into consideration the fact that the reflection intensity varies on the mask from place to place, in addition to which the number of photons needed to facilitate detection of signals from defects is several orders greater than the number calculated by equation (2). Decreasing the is amount of tune allocated to exposure to reduce the time required for processing the data, results in an increase in the power that is needed. How much power is actually required is something that has to be determined through future empirical investigation, but it is feared that more than a watt of power will be required.

As can be seen from equation (1), the number of photons required can be decreased by bringing the size of the pixel $S_{pix}$ closer to the size of the target defect $S_{def}$. Assuming the same reflectance, if a pixel size of 90 nm was used, then $(nS_{def})\geq 5,700$, meaning it would be possible to reduce the required power to one-fifth.

However, because light cannot be focused to below its diffraction limit, the wavelength of the illuminating laser beam has to be shortened in order to decrease the size of the beam, meaning the size of the pixel. However, it is not easy to decrease the laser wavelength to below 200 nm. Because it is so difficult to achieve continuous laser oscillation at or below a wavelength of 250 nm directly, attempts have been made at achieving shorter wavelengths by the wavelength conversion of 266-nm light, but the conversion decreases the power, in addition to which, based on such factors as the power resistance of the wavelength conversion crystals, at present it is only possible to obtain power in the microwatt to sub-milliwatt order. Even when the power needed for inspection is reduced by reducing a pixel size using a short wavelength laser, if decrease of the available power for shorting wavelength of the laser wavelength is greater than the decrease of the power for inspection, it is better not to reduce the laser wavelength. That is to say, detecting ultrasmall defects is difficult when the illumination used is of a wavelength that provides poor contrast between the reflectance of the substrate and that of the pattern.

If the wavelength of the inspection light is the peak wavelength of the reflection spectrum of the multilayer mask, the contrast ratio between the signal from the inspection target and the signal from the background can be large to make detection of small defects easier. However, if the inspection is performed in the bright field configuration so that $R_{def}$ is small and the substrate reflectance $R_{pix}$ is large, as can be understood from equation (1), no major improvement in contrast ratio can be achieved. In order to achieve a jumping improvement in the contrast ratio, it is important to increase the signal from defects and decrease the signal from the background. If, for example, a defect produces an effective reflectance $R_{def}$ of 0.6 and the background effective reflectance $R_{pix}$ can be reduced to 0.001, even if the size of the pixel is as large as 3 μm, equation (1) gives the number of photons needed to detect a 30-nm defect.

$$(nS_{def}) \geq 1{,}030 \quad (3)$$

in this case, $I_{def}$=10,920 and $I_{pix}$=10,300, so the difference in intensity is as large as 6%, facilitating the determination of whether there is or is not a defect.

In the case of the use of the laser described above, at $(nS_{def}) \geq 27{,}800$, some 30 times more photons are required, and, moreover, there is only a 1% difference between the intensities of signals from a pixel that includes a defect and a pixel that does not include a defect. It also has to be noted that that was the calculation in the case of a 200-nm pixel size, which is just 1/200 the size of a 3 μm pixel, This shows the great effectiveness of decreasing the background signal.

Large value for the reflectivity $R_{def}$ by defects and small reflectivity $R_{pix}$ for the background can be achieved in tie dark-field configuration, in which specularly reflected light is blocked.

When $U_1$ is the light wave observed at the observation point when a masking shield is provided between the light source and the observer, and $U_2$ is the light wave when the aperture is placed in precise registration with the masking shield, and $U_0$ is the light wave when there is nothing therebetween, based on the Babinet principle, $U_1+U_2=U_0$. If a disposition is used that blocks specularly reflected light, then $U_0=0$, therefore $U_1=-U_2$, in which case the intensity $|U_1|^2$ of the scattered light signals shielded by a defect is equal to the intensity $|U_2|^2$ of the light transmitted from the aperture in precise registration with the defect. That is, in the dark-field observation, $R_{pix}$ will be substantially zero, and $R_{def}$, which determines scattered light intensity from a defect, will be equal to the reflectance of the substrate mask.

Yi et al. conducted tests using the dark-field configuration (J. Vac. Sci. Tech. B18 (2000) 2930). A microbeam measuring 2.5 μm by 4 μm was formed by focusing a synchrotron beam using a grazing incidence KB mirror configuration on which reflected 13-nm EUV fell incident at a glancing angle. The beam was used to illuminate programmed defects, and an MCP detector was used to detect scattered light from the defects. The MCP detector, which had an outside diameter of 44 mm and a central opening with a diameter of 4.7 mm, detected scattered light, without detecting specularly reflected light. The collection solid angle of the detector was 0.068 rad. With this arrangement, they claimed 60-nm defects on the multiplayer were detected. Thus, with the dark-field observation, it was possible to obtain a great improvement in the detection sensitivity of small defects, enabling actual detection of a 60-nm defect in a large pixel size of 2.5 μm by 4 μm. That is, it was possible to measure a small defect with an area ratio of 2800:1.

However, they reported that it took 30 hours to scan a region of 1 cm². To be of practical utility, it is necessary to be able to inspect a 140 mm by 140 mm mask in two or three hours. This means we need to improve the inspection speed by three orders of magnitude. Moreover, even if a high speed were to be realized, their synchrotron light facility would be too large and costly for practical lithographic application.

In view of the above drawbacks of the prior art, an object of the present invention is to provide a method and apparatus for inspecting multilayer masks for small defects difficult to detect with means using visible or ultraviolet lasers, with inspection speed faster more than three orders of magnitude of the speed reported by the prior works using a synchrotron source.

Another object is to provide a method and apparatus for inspecting multilayer masks for defects that employ a light source that is compact and can be readily utilized by anyone.

SUMMARY OF THE INVENTION

To attain the above object, the present invention provides a method for inspecting multilayer masks for small defects, comprising: illuminating a region of a mask to be inspected, using illuminating light having a near peak wavelength of a reflection spectrum of the mask; blocking illuminating light specularly reflected by the mask and collecting scattered reflected illuminating light to form an enlarged image; and using an image detector having a large plurality of pixels to observe the enlarged image to thereby detect small defects on the mask.

The above method also includes observation while blocking a specific angular distribution scattering component.

The above method also includes use of a Schwarzschild optical system comprising convex and concave mirrors to collect the scattered reflected illuminating light and form an enlarged image.

The above object is also attained by an apparatus for inspecting multilayer masks for defects, comprising: a plasma light source for generating radiant rays having a near peak wavelength of a reflection spectrum of the mask; an illuminating light collecting optical system that collects radiated light from the light source for enlarged image formation illumination of a subject inspection region; a Schwarzschild optical system comprising convex and concave mirrors for collecting scattered light, with specularly reflected light blocked, from the subject inspection region and forming an enlarged image of the inspection region; an image detector having a large plurality of pixels for recording the enlarged image that is obtained; and analysis means for determining from the obtained image whether or not there is a defect.

The above apparatus also includes a reflector provided on a back surface of the convex mirror to guide illuminating light to the subject inspection region and located at a position where it does not interfere with collecting of scattered light from the inspection region by the Schwarzschild optical system.

The above apparatus also includes a plate for controlling angular distribution of scattered collected light for observation by blocking scattered light having a specific scattering angle, the plate being provided on an optical path of the scattered light.

By using a Schwarzschild optical system that enables a sufficient large magnification, an image detector having a large plurality of pixels and a plasma light source, the present invention makes it possible to detect small defects that are difficult to detect by methods that use visible or ultraviolet lasers, and can perform the defect inspection not less than one hundred times faster than the prior art using a synchrotron source. Moreover, since a plasma light source is used, the apparatus can be made more compact.

The above objects and further features of the invention, its nature and various advantages will be more apparent from the accompanying drawings and following detailed description of the invention.

DESCRIPTION OF THE PREFERRED EMBODIMENT

Figure 1:
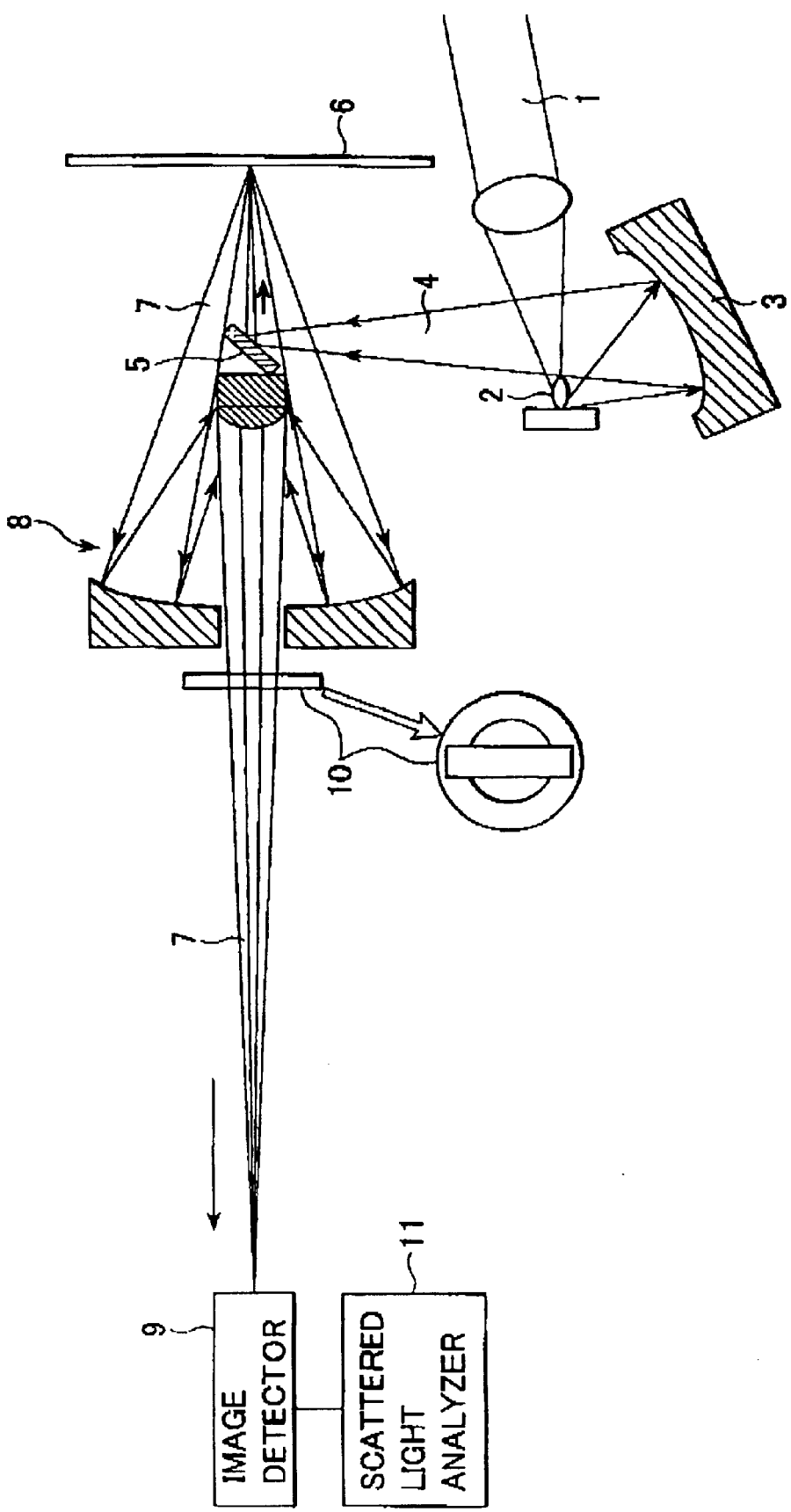
FIG. 1 is a schematic view of one embodiment of an optical system of an apparatus for inspecting multilayer masks for defects, according to the present invention.

The present invention was perfected, as described below, after carrying out various considerations on inspection of defects on a multiplayer mask.

Specifically, as described above, dark-field observation makes it possible to detect defect-based signals with a very high contrast ratio, so that, as is clear from equation (1), it is possible to detect small defects within a large pixel. For the dark-field observation, it is necessary to use a light source having a wavelength that is near the peak of reflection spectrum of the multilayer reflective mask. As mentioned in the foregoing, Yi et al. demonstrated that it was possible to detect small defects within a large pixel in the dark-field observation with a synchrotron light source. However, the speed of the inspection by the method of Yi et al. was in the order of 1,000 times slower that what is needed in practice. Analyses carried out by the present inventors showed the reasons for this, which reasons are explained below.

The first reason is that, because one observation is of one pixel, the exposure time allocated to one pixel is very short. In the case of Yi et al., the microbeam size (meaning the size of one pixel) was 2.5 µm by 4 µm, meaning 1E9 movements would be required to inspect the whole of a mask measuring 140 mm by 140 mm. When the scanning is finished in one hour, each move has to take no longer than 3 µs. Thus, each pixel exposure has to be completed in less than 3 µs, which requires a very bright light source.

The second reason is that one pixel is too large. The dark-field method makes it possible to obtain high-contrast observations. However, although very weak, there exists also scattered light, arising from substrate non-uniformity, so in order to increase the contrast ratio of very small defect signals, one pixel should be made as small as possible.

The present invention was accomplished from such analyses. To ensure an adequate supply of photons, using the brightest possible light source, the number of pixels observed at one time was increased and the pixel exposure time increased. Also, to raise the contrast ratio of signals from very small defects, an enlarged image of the subject inspection region was formed on a two-dimensional image detector, to carry out observations using a smaller pixel size.

In the case of the present invention, first, in order to increase the number of pixels observed at one time, 13-nm EUV light was used to illuminate a region corresponding to, for example 1,000 by 1,000 500-nm pixels, meaning an area of 0.5 mm by 0.5 mm was illuminated each time, and scattered light from the whole region used to form an image on the image detector. When the size of the region per inspection scan is increased to this extent, it takes 4E4 movements to complete the inspection scanning of an entire 140 mm by 140 mm mask. When the inspection should be finished in one hour, an exposure of as long as 0.1 second per region is allowed. Being able to increase the exposure time greatly reduces the power demands on the light source.

Second, with respect to the method of collecting scattered light, the present invention uses an optical system with a sufficiently high magnification for forming the scattered light image. If the size of the light-receiving surface is 25 mm by 25 mm, for example, the size of one pixel of a 1,000-by-1,000-pixel image detector is 25 µm, but if the size of the image formed on the image device is increased by an enlargement ratio of 80, the size of one pixel on a mask to be inspected is 300 nm. By reducing the pixel size of the inspection region in this way, the contrast ratio of signals from very small defects can be increased.

If, for example, the mask substrate has a reflectance of 0.6, $R_{def}$=0.6 in the dark-field method. If the background reflectance in the dark field configuration is assumed to be $R_{pix}$=0.001 caused by the surface roughness of the substrate mask, when the size of a defect to be detected is 30 nm and the size of one pixel is 300 nm, then:

$$(nS_{def}) \geq 33 \tag{4}$$

At this time, $I_{def}$=23.3 and $I_{pix}$=3.3, so the contrast ratio, that is, the intensity of one is seven times more than the other, making it very easy to determine the presence or absence of defects. Looking at equation (3), thirty times more photons were required in the case of a single pixel size of 3 µm, and the signal differential was only 6%.

In order to collect light scattered at a large angle and also to decrease the size of a single pixel to be inspected, the present invention uses a Schwarzschild optical system (SO) comprising a combination of convex and concave mirrors. To collect light scattered by a 30 nm defect (total angle of divergence $\theta$ ($\sin(\theta/2)$ in the order of 0.4), the SO was given a numerical aperture (NA) in the order of 0.2. Light scattered toward the back surface of the convex mirror (NA=0.2) is not collected to form an image, so the specularly reflected light is shielded, resulting in dark-field observation. Scattering components with a small scattering angle arising from mild non-uniformity of the mask are also blocked, improving the signal-to-noise ratio of signals from defects.

The SO is an enlargement optical system that can form an enlarged image of scattered light from the inspection region on the two-dimensional image detector. If the SO has an enlargement ratio of ×80, the image detector has a 25-mm light-receiving surface and there are 1,000×1,000 pixels, with a mask observation region measuring 0.3 mm, the size of a single pixel inspected on the mask will be 300 nm. When the background signal level can be decreased and the pixel size increased, the pixel size can be set to 1 µm, for example, the mask observation region can be set at 1 mm, and an enlargement ratio of ×25 selected.

How large a single pixel can be made depends on the intensity $R_{pix}$ of noise due to non-uniformity of the substrate mask. If the $R_{pix}$ value is low, such as 0.001, even if a pixel size of as large as 1 µm is used, $(nS_{def}) \geq 130$, $I_{def}$=207 and $I_{pix}$=129 based on equation (1), and it would be easy to differentiate the signals. However, if there was ten times more noise making an $R_{pix}$ value of 0.01, then $(nS_{def}) \geq 1,064$, $I_{def}$=11,300 and $I_{pix}$=10,600. A signal intensity differential of 7% would make it possible to differentiate the signals, but not at a glance, and it would require some slightly complex data analysis. Even with a high $R_{pix}$ of 0.01, when a pixel size is reduced to 0.3 µm, $(nS_{def}) \geq 132$, $I_{def}$=211 and $I_{pix}$=132, facilitating differentiation. When there is a large substrate mask noise component, it is necessary to reduce the inspected pixel size.

Third, with respect to the light source and method of illumination, the present invention uses a light source that has the large product of the source beam and angle of divergence. To speed up the inspection, it is important to simultaneously observe numerous pixels, which requires a light source able to brightly illuminate an extensive region. If, for example, a single inspection pixel on the mask is 300 nm, the size of a region of 1,000×1,000 pixels would be 0.3 mm by 0.3 mm. For the brightest possible illumination the light source should have a large convergence angle, but for dark-field observation, there is an upper limit to the convergence angle, which is now 0.1 rad. Thus, the product of the size of the illuminated region and the convergence angle of the illuminating light will be 0.3 mm×0.1 rad. In optical image-relay, the product of image size and angle of divergence is maintained, so the product of the source beam size and the collection angle of the optical system that collects light rays emitted by the source will also be equal to 0.3 mm×0.1 rad. In the case of a 50-$\mu$m plasma beam generated by a pulsed laser, the collection angle will be 0.6 rad.

The time-integrated power of the radiant light per unit solid angle is tens to hundreds of times greater than that of a laser plasma light source. However, due to the small angle of divergence in the order of 1 mrad of the synchrotron light source, there is no increase in power even when an optical collection system is used, but because a plasma light source is a divergent point light source, increasing the solid angle collection increases the collected power. If a 50-$\mu$m plasma-beam is collected up to an angle of 600 mrad, the product of light source area and solid angle of divergence will be 3.5 digits greater than that of the synchrotron light source. Therefore, contrary to what is generally believed, at a certain repetition rate, a plasma light source can provide brighter illumination of the mask than a synchrotron source.

As shown in FIG. 1, a plasma light source 2 produces a beam of EUV light 4 that is used for mask inspection. The EUV light 4 is deflected onto a mask 6 by a multilayer reflector 5 provided on the back surface of a convex mirror of a SO 8. The light collected by the SO 8 is light scattered beyond the outer periphery of the convex mirror, so the multilayer reflector 5 has no effect on the SO image formation. The mask 6 illumination numerical aperture NA is highest from the inspection region to the convex mirror, but an NA of around 0.1 is possible. A larger NA means a brighter mask illumination, but since the light source has brightness to spare, it is also possible to reduce the NA to around 0.015.

Figure 2:
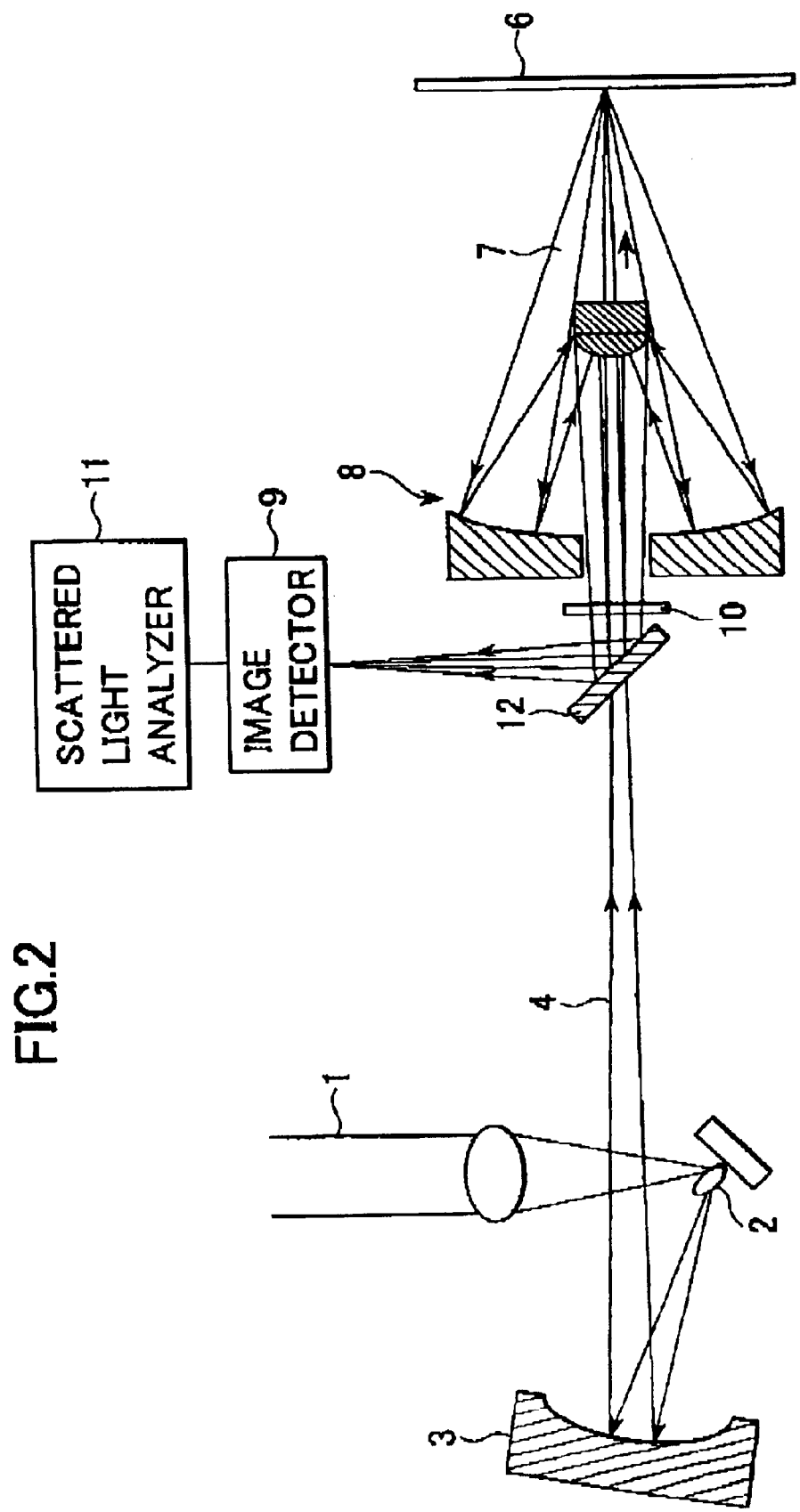
FIG. 2 is a schematic view of another embodiment of an optical system of an apparatus for inspecting multilayer masks for small defects, according to the present invention.

The illuminating EUV light used for the inspection can be introduced by the following method. The pattern of scattered light from the mask 6 collected by the SO 8 is in the shape of a doughnut with a hole at the center where the shadow of the convex mirror falls. This hollow center portion can be utilized. For example, as shown in FIG. 2, the convex mirror of the SO 8 is provided with a central through-hole, whereby the EUV light 4 from the plasma light source 2 is guided to the mask 6 by the central through-holes in the convex and concave mirrors of the SO 8. If a multilayer reflector 12, which has a hole, is used to guide doughnut-shaped reflected light 7 from the mask 6 to an image detector 9, the EUV light that passes through the hole in the multilayer reflector 12 can be used to illuminate the inspection region. Although in this case the concave mirror has to be provided with a through-hole, this does not affect the image-formation characteristics of the SO.

In the arrangement of FIG. 2, restrictions are imposed on the NA determined by the distance of the convex mirror of the SO from the mask and the size of the hole of the doughnut-shaped pattern of the light when collected by SO and then passing through the concave mirror, resulting in an NA of around 0.05 smaller than that in the case of the arrangement of FIG. 1 in which the reflector is placed behind the convex mirror. However, the light source having this NA can sufficiently be used.

Compared to the arrangement of FIG. 1 in which the reflector is positioned in the small space between the convex mirror and the mask, plenty of space can be provided between the concave mirror and the mask, increasing the design freedom of the SO and specimen stage.

Next, the brightness required of the light source is calculated. Equation (4) tells us that, with a pixel size of 300 nm, to detect a 30-nm defect, the 30-nm area has to be illuminated by 33 photons. In the case of a pixel size of 500 nm, 54 photons would be needed, and 130 photons in the case of a 1-$\mu$m pixel.

If the pixel size is 0.5 $\mu$m and radiation of 54 photons per 30-nm area is used, 2E13 times that number are needed to illuminate a mask measuring 140 mm by 140 mm, meaning 1E15 photons. If 0.5 hour of the inspection time is allocated for illumination, a photon flux of 6E11/sec is required. For light source collection, reflection to the SO and image detector and so forth, a multilayer consisting of four layers is used. If each layer has a reflectance of 60%, the product of the reflectance will be 13%, in which case it will be necessary to collect 4.6E12 photons per second from the light source. If 1,000×1,000 pixels are observed at one time, the size of the illuminated region on the mask will be 0.5 mm by 0.5 mm. An illumination convergence angle of 200 mrad is used. Since the product of the light source beam size and collection angle also is 0.5 mm×200 mrad, to collect 4.6E12 photons per second, the light source brightness B$_{average}$ defined by the number of photons discharged per unit area, unit solid angle and unit time has to be at least $$B_{average}=4.6E8 \text{ photons}/(\text{sec mm}^2 \text{ mrad}^2 \text{ 1\% } BW) \quad (5)$$

The bandwidth of the multilayer reflection spectrum is in the order of 2%, so in equation (5), 1% BW is used to signify the number of photons required per 1% of spectrum bandwidth.

In the case of a plasma light source, the following peak brightness B$_{peak}$ is readily obtained.

$$B_{peak}=1E16 \text{ photons}/(\text{sec mm}^2 \text{ mrad}^2 \text{ 1\% BW}) \quad (6)$$

If 10 ns is the pulse width of the pulsed laser used to generate the plasma, the number of photons per shot will be $$B_{peak}=1E3 \text{ photons}/(\text{shot mm}^2 \text{ mrad}^2 \text{ 1\% BW}) \quad (7)$$

Therefore, with a scanning frequency of 10 Hz, the number of photons required to illuminate 1 pixel, can be obtained in one illumination shot. The plasma can be generated at a repetition rate of not less than 100 Hz. If necessary, through future research and development, the repetition rate can be raised to several kilohertz, giving the light source a margin of brightness in the order of two to three digits.

A consideration on the reading out pixel information of the image detector showed that the smallest pixel size depends on the image-processing rate. If the mask region observed each time measures 0.5 mm along each side, 8E4 observations will be required to inspect an of a mask measuring 140 mm by 140 mm. When the whole mask is inspected, if 1 hour is allocated for reading images, each image area has to be read in not more than 1/22 second. If the image detector has 1,000×1,000 pixels, an image read rate of 22 MHz is required. Since there are two-dimensional image detectors that are already able to operate at 10 Mz, an adequate image read rate is ensured.

The image read rate has to be increased in order to decrease the pixel size. Barring difficulties, the development of devices that operate at a 100 MHz read rate can be expected, which will make it possible to reduce the pixel size to 240 nm It is also not so difficult to achieve an SO resolution of 240 nm. The image detector has to be highly sensitive to 13-nm EUV light, which is no problem since there are high-sensitivity background illumination type CCD cameras that have an EUV light quantum efficiency that is dose to 1. A CCD camera has a pixel size in the order of 25 $\mu$m; if the SO is used to effect a ×50 image enlargement, the pixel size on the mask would be 0.5 $\mu$m.

In the case of a multiplayer reflector, high reflectance is obtained by interference between lights reflected from the many interfaces, so the reflectance peak wavelength depends on the angle of incidence. The relationship between interlayer distance d, angle of incidence $\theta$ and reflection peak wavelength $\lambda$ is $$d \cos \theta = \lambda \tag{8}$$

The angular dependency of the multilayer peak wavelength does have an effect in the case of this invention, as follows.

First, with respect to the collection of scattered light, light scattering from the region of inspection is reflected first by the concave mirror of the SO, then by the convex mirror, and is thereby deflected to the image detector. The light falling incident on the concave and convex mirrors is substantially perpendicular. Depending on the location, the angle of incidence will differ by a few degrees; a difference of a few degrees poses virtually no problem, as explained below. However, if necessary, variations in the reflection peak based on the positions of the concave and convex mirrors can be suppressed by using vapor deposition to modify the interlayer distance according to the positions of the mirrors.

Next, with respect to the effect on the illumination, illumination with a high numerical aperture NA is desirable from the standpoint of obtaining the brightest illumination. In the case of a NA of 0.1, the mask is illuminated at a maximum angle of incidence $\theta$ of 0.1 rad Based on equation (8), the peak reflection wavelength in the case of an incidence of $\theta$=0.1 rad will be 0.5% shorter than in the case of perpendicular incidence. The bandwidth of the reflection spectrum of the multilayer is in the order of 2%, an amount of deviation that poses no problem whatsoever.

The 1% difference in peak reflection wavelength compared to the wavelength in the case of perpendicular incidence is that of the angle of incidence of 0.14 rad. Should it become necessary to use a high numerical aperture illumination, since there is just the one mask constituted by the multilayer on which the light falls obliquely incident, the reduction in light intensity is so slight that it does not pose a problem.

Next, eliminating the effect of scattered light by patterns without defects will be described. Light is scattered by the circuit pattern defined on the mask. To facilitate the detection of defects, it is necessary to suppress the inclusion of light scattered by patterns without defects. Light scattered by a pattern is scattered in a direction orthogonal to the direction of longitudinal pattern formation. The angles at which light is scattered by a circuit pattern are limited. If the circuit pattern is known, the angle at which light is scattered can be calculated. The effect of normal pattern scattered light can be eliminated if light of those specific angular components is prevented from reaching the image detector. This can be done by fabricating an angle mask that blocks light of the specific angles concerned, and positioning the mask in the vicinity of the central opening in the concave mirror of the SO, for example.

Based on the fundamental concept described above, the present invention can be implemented by, for example, using the optical system outlined in FIG. 1. That is, laser pulses 1 are used to generate EUV light from the plasma light source 2. An enlarging/illumination optical system 3 is used to collect the EUV light. The multiplayer reflector 5 reflects the illumination light 4 thus collected to illuminate the inspection region on the reflective mask 6.

The pulse width of the laser 1 is set at 10 ns, for example. When the size of the plasma light source 2 is 50 $\mu$m, the collection angle of the optical system 3 is 0.6 rad, and the illuminating light 4 is enlarged by a ratio of ×6, a 0.3-mm region on the mask will receive the illumination of a numerical aperture NA of 0.05. If there is a defect within the pixel, scattered light 7 produced by the defect is collected by the SO 8 and forms an enlarged image on the two-dimensional image detector 9.

If the size of the defect is 30 nm, the light scattered by the defect will have a divergence of about 0.4 rad. To ensure that virtually all of this light is collected, the SO 8 is given a numerical aperture NA of, for example, 0.2. The convex mirror of the SO 3 blocks specularly reflected illumination light in the case of a NA of 0.05, so that only light scattered at a large angle is collected. If the enlargement ratio of the SO 8 is set at ×80, for example, the 0.3-mm region on the mask will be transferred to the whole of the 25-mm light-receiving surface of the image detector 9. If an image detector 9 with 1,000×1,000 pixels is used, single pixels measuring 300 nm on the mask can be inspected. If the mask is designed for 13-nm EUV light, observation under bright illumination can be carried out through use of vapor deposition to also form a 13-nm-EUV-light reflecting multilayer on the optical system 3, reflector 5 and SO 8.

To reduce the effect of scattered light from normal mask patterns and thereby make it easier to detect defects, the light is passed through an angular distribution control plate 10 for image formation. A scattered light analyzer 11 is used to analyze images obtained with the image detector 9, to determine the presence or absence of defects. Although illumination of a sufficient intensity can be obtained with one shot of laser pulses 1, if required, multiple exposure shots can be used and the images obtained stored in the image detector 9. If the image detector 9 is operated at an image read frequency of 10 MHz, the reading of the 1,000× 1,000 pixels will be completed in 0.1 second The mask is moved to inspect one 0.3-mm-by-0.3-mm region at a time. Scanning of a mask measuring 100 mm by 100 mm is completed after 100,000 observations. Inspection of one mask takes about 3 hours.

The foregoing description is one example of the pulse width of the laser pulses 1 used to produce the plasma, the size of the plasma light source 2, the collection angle and enlargement ratio of the illuminating optical system 3, the size of the illuminated region on the mask 6, the illumination numerical aperture, the enlargement ratio and collection numerical aperture of the SO 8, the size of the light-receiving surface of the image detector 9, the number of pixels and the pixel read rate. Thus, it is to be understood that combinations of other numerical values can also be used.

The positional relationship of the laser pulses 1, plasma light source 2, optical system 3, mask 6 and Schwarzschild optical system 8 shown in FIG. 1 is only used to show an outline of the configuration of the inspection apparatus. It is not meant to show what the positional relationship of the components will be in practice, which can differ so long as in the arrangement used, the illuminating light is directed onto the mask under inspection.

The angular distribution control plate 10 is shown positioned directly behind the Schwarzschild optical system 8. However, it can be placed elsewhere, such as in front of the convex mirror where the intensity of scattered light from defects is higher, or at any other desired location on the scattered light path.

Moreover, further explanation of the optical system shown in FIG. 2 is omitted since it goes without saying that, as in the case of the optical system shown in FIG. 1, it can be used to carry out inspections to detect defects in multilayer masks.

The above-described means used in accordance with the present invention to inspect multilayer reflective masks for small defects, uses radiant light to detect small defects that are difficult to detect with visible or ultraviolet light. In addition, the inspection can be carried out not less than one hundred times faster than in the prior art. Also, the invention uses a light source, such as a plasma light source, which is compact and can be readily used by anyone.

What is claimed is:

1. A method for inspecting multilayer masks for small defects, comprising:

illuminating a region of a mask to be inspected using illuminating light having a near peak wavelength of a reflection spectrum of the mask;

collecting scattered reflected illuminating light to form an enlarged image with illuminating light specularly reflected from the mask being blocked by a Schwartzschild optical system and an angular distribution control plate outside an optical system for collecting scattered reflected illuminating light including a structure of the optical system; and using image detector having a large plurality of pixels to observe the enlarged image to there y detect small defects on the mask.

2. The method according to claim 1, wherein observation is performed while blocking a specific angular distribution scattering component.

3. The method according to claim 1, further comprising use of a Schwarzschild optical system comprising convex and concave mirrors to collect the scattered reflected illuminating light and form an enlarged image.

4. The method according to claim 1, with the product of size of the illuminated region on the inspected multilayer mask and illumination numerical aperture NA being larger than 0.3 mm×0.015.

5. An apparatus for inspecting multilayer masks for defects, comprising:

a plasma light source for generating radiant rays;

an illuminating light collecting optical system that collects radiated light from the light source for enlarged image formation illumination of a subject inspection region;

a Schwarzschild optical system comprising convex and concave mirrors for collecting scattered light from the subject inspection region and forming an enlarged image of the inspection region;

an optical system to guide illuminating light having a near peak wavelength of a reflection spectrum of the mask to the subject inspection region so that specular reflection of the illuminating light by the inspected multilayer mask is blocked by the convex mirror of the Schwarzschild optical system for collecting scattered light from the subject inspection region;

an image detector having a large plurality of pixels for recording the enlarged image that is obtained; and analysis means for determining from the obtained image whether or not there is a defect.

6. The apparatus according to claim 5, further comprising a reflector provided on a back surface of the convex mirror to guide illuminating light to the subject inspection region and located at a position where it does not interfere with collecting of scattered light from the inspection region by the Schwarzschild optical system.

7. The apparatus according to claim 5, further comprising a plate for controlling angular distribution of scattered collected light for observation by blocking scattered light having a specific scattering angle, said plate being provided on an optical path of the scatter light.

8. The apparatus according to claim 6, further comprising a plate for controlling angular distribution of scattered collected light for observation by blocking scattered light having a specific scattering angle, said plate being provided on an optical path of the scattered light.

* * * * *